United States Patent
Bretthauer et al.

(10) Patent No.: US 10,641,626 B2
(45) Date of Patent: May 5, 2020

(54) MEMS SENSORS, METHODS FOR PROVIDING SAME AND METHOD FOR MEASURING A FLUID CONSTITUENT

(71) Applicant: Infineon Technologies AG, Neubiberg (DE)

(72) Inventors: Christian Bretthauer, Munich (DE); Alfons Dehe, Villingen-Schwenning (DE); Prashanth Makaram, Munich (DE); Abidin Güçlü Onaran, Munich (DE); Arnaud Walther, Unterhaching (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 10 days.

(21) Appl. No.: 16/106,247

(22) Filed: Aug. 21, 2018

(65) Prior Publication Data
US 2019/0063968 A1    Feb. 28, 2019

(30) Foreign Application Priority Data

Aug. 23, 2017    (DE) .......................... 10 2017 214 786

(51) Int. Cl.
| | | |
|---|---|---|
| G01F 1/36 | (2006.01) | |
| G01F 1/38 | (2006.01) | |
| G01F 1/84 | (2006.01) | |
| G01K 7/32 | (2006.01) | |
| G01N 33/00 | (2006.01) | |
| G01N 29/32 | (2006.01) | |
| G01N 29/036 | (2006.01) | |
| G01N 29/30 | (2006.01) | |
| G01N 29/02 | (2006.01) | |

(Continued)

(52) U.S. Cl.
CPC .............. *G01F 1/363* (2013.01); *G01F 1/383* (2013.01); *G01F 1/84* (2013.01); *G01K 7/32* (2013.01); *G01L 9/0016* (2013.01); *G01L 19/0092* (2013.01); *G01N 11/08* (2013.01); *G01N 29/022* (2013.01); *G01N 29/036* (2013.01); *G01N 29/30* (2013.01); *G01N 29/323* (2013.01); *G01N 29/326* (2013.01); *G01N 33/0009* (2013.01); *G01N 2291/0256* (2013.01); *G01N 2291/02809* (2013.01)

(58) Field of Classification Search
CPC ................. G01F 1/36; G01F 1/38; G01F 1/84
See application file for complete search history.

(56) References Cited

U.S. PATENT DOCUMENTS

| | | | | |
|---|---|---|---|---|
| 9,102,519 B2 * | 8/2015 | Dehe | .................... | B81C 1/00182 |
| 9,510,107 B2 * | 11/2016 | Dehe | .................... | H04R 19/005 |

(Continued)

FOREIGN PATENT DOCUMENTS

| | | |
|---|---|---|
| DE | 69827767 T2 | 3/2006 |
| DE | 102015110711 A1 | 1/2017 |

*Primary Examiner* — Jewel V Dowtin
(74) *Attorney, Agent, or Firm* — Slater Matsil, LLP

(57) ABSTRACT

In accordance with an embodiment, a MEMS sensor includes a membrane that is suspended from the substrate, a resonant frequency of said membrane being influenced by an ambient pressure that acts on the membrane; and an evaluation device configured to perform a first measurement based on the resonant frequency of the membrane to obtain a measurement result, where the evaluation device is configured to at least partly compensate an influence of the ambient pressure on the measurement result.

25 Claims, 8 Drawing Sheets

(51) Int. Cl.
*G01L 9/00* (2006.01)
*G01L 19/00* (2006.01)
*G01N 11/08* (2006.01)

(56) References Cited

U.S. PATENT DOCUMENTS

| | | | |
|---|---|---|---|
| 10,322,481 B2* | 6/2019 | Dehe | B23Q 3/18 |
| 10,330,511 B2* | 6/2019 | Alkhabbaz | G01F 1/7046 |
| 2019/0041363 A1* | 2/2019 | Tumpold | G01N 29/2425 |

* cited by examiner

| Type | Membrane size | f₀ [MHz] |
|---|---|---|
| 1 | 13.2 μm | ~31-32 |
| 2 | 13.2 μm | ~31-32 |
| 3 | 20 μm | ~17 |
| 4 | 12.6 μm | ~34 |

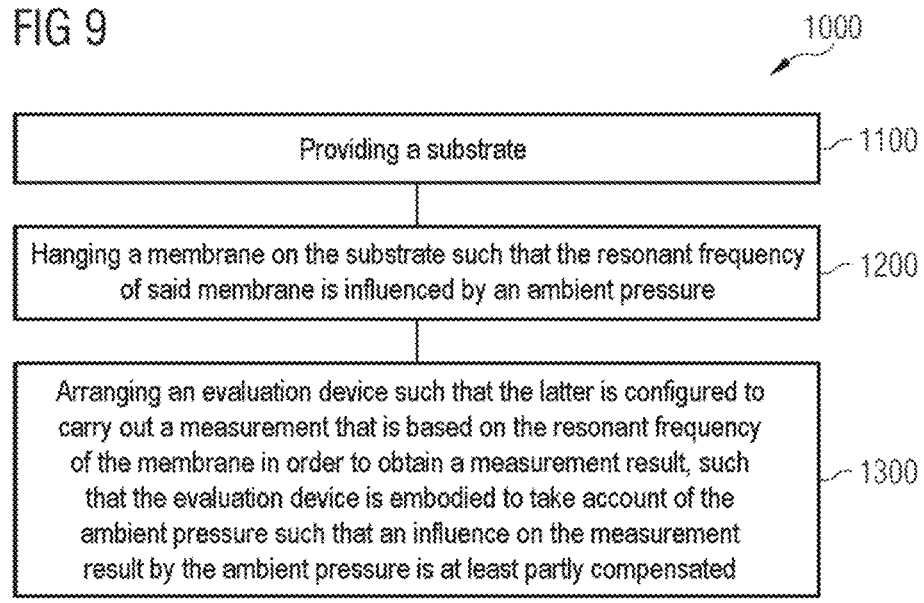
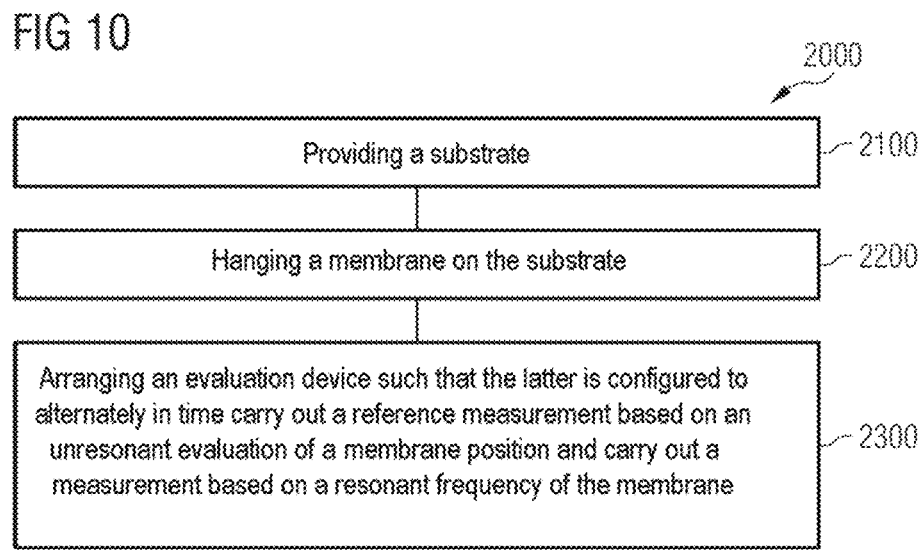

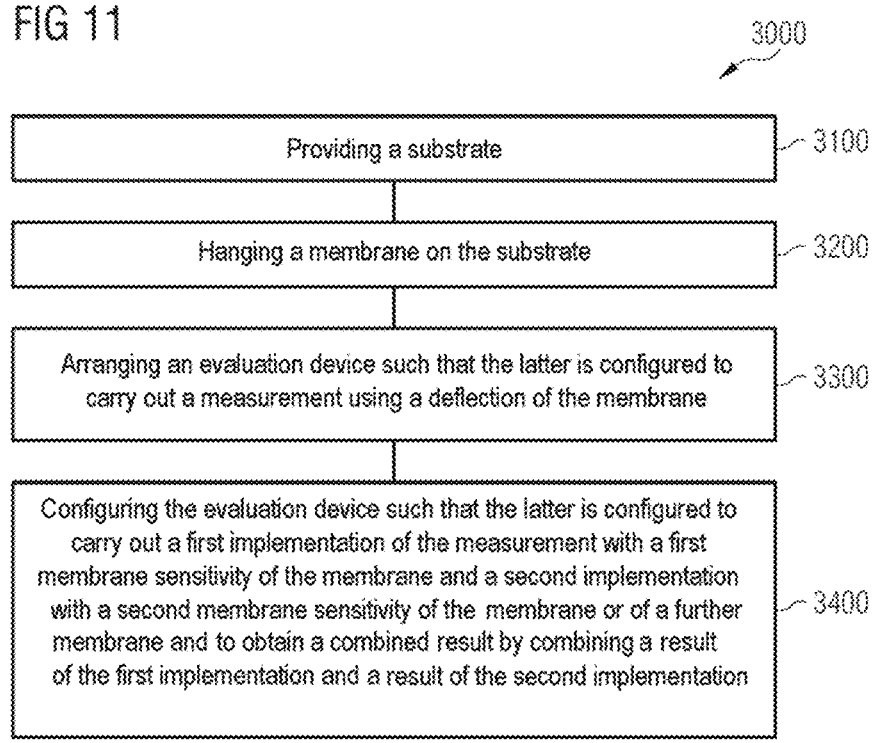

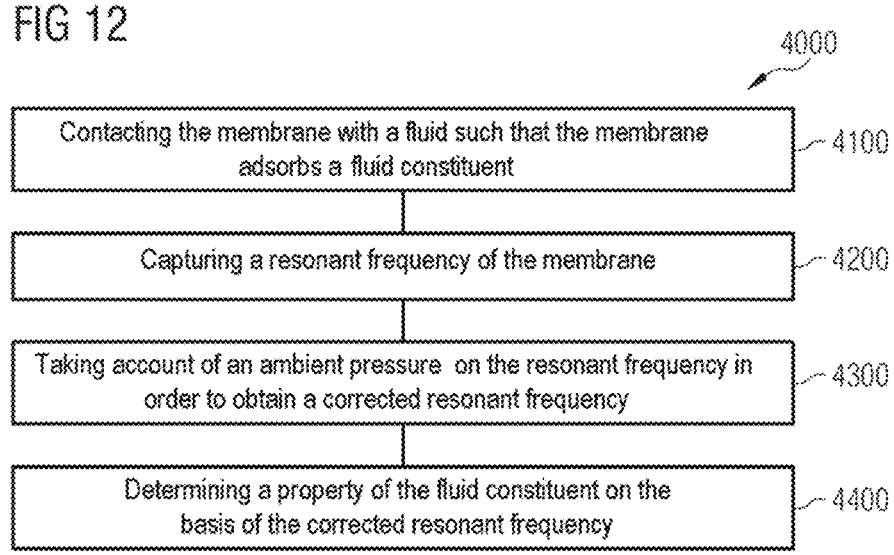

US 10,641,626 B2

MEMS SENSORS, METHODS FOR PROVIDING SAME AND METHOD FOR MEASURING A FLUID CONSTITUENT

This application claims the benefit of German Application No. 10 2017 214 786.5, filed on Aug. 23, 2017, which application is hereby incorporated herein by reference in its entirety.

TECHNICAL FIELD

The present disclosure relates to MEMS sensors, in particular MEMS sensors for capturing a fluid constituent, for instance gas sensors, to methods for providing same and to a method for measuring a fluid constituent.

BACKGROUND

MEMS pressure transducers (micro-electromechanical systems) can be manufactured using semiconductor technology and/or can comprise semiconductor materials. These include, for example, layers or wafers comprising a silicon material, a gallium arsenide material and/or another semiconductor material. MEMS structures may have sequences of layers which comprise electrically conducting, electrically semiconducting and/or poorly electrically conducting or insulating layers in order to provide a corresponding MEMS functionality. Some MEMS sensors can be implemented as pressure transducers, meaning that an electrical signal is output on the basis of a static (pressure sensor) or dynamic (microphone) pressure change and/or a pressure wave is produced in a fluid in response to an electric signal.

Further, membranes in MEMS sensors can be usable for fluid sensors, in which an interaction between a fluid and a membrane is evaluated in order to deduce the fluid.

SUMMARY

According to an exemplary embodiment, a method for providing a MEMS sensor includes providing a substrate, hanging a membrane on the substrate such that the resonant frequency of said membrane is influenced by an ambient pressure, and arranging an evaluation device such that the latter is configured to perform a measurement that is based on the resonant frequency of the membrane in order to obtain a measurement result and such that the evaluation device is embodied to take account of the ambient pressure such that an influence on the measurement result by the ambient pressure is at least partly compensated.

According to an exemplary embodiment, a method for providing a MEMS sensor includes providing a substrate and hanging a membrane on the substrate and arranging an evaluation device such that the latter is configured to alternately in time perform a reference measurement based on an unresonant evaluation of a membrane position and perform a measurement based on a resonant frequency of the membrane.

According to an exemplary embodiment, a method for providing a MEMS sensor includes providing a substrate, hanging a membrane on the substrate, and arranging an evaluation device such that the latter is configured to perform a measurement using a deflection of the membrane. The method includes configuring the evaluation device such that the latter is configured to perform a first implementation of the measurement with a first membrane sensitivity of the membrane and a second implementation of the measurement with a first membrane sensitivity of the membrane and a second implementation of the measurement with a second membrane sensitivity of the membrane or of a further membrane and to obtain a combined result by combining a result of the first implementation and a result of the second implementation.

According to an exemplary embodiment, a method for measuring a fluid constituent with a fluid sensor having a membrane that is suspended from a substrate includes contacting the membrane with a fluid such that the membrane adsorbs a fluid constituent, capturing a resonant frequency of the membrane, taking account of an ambient pressure on the resonant frequency in order to obtain a corrected resonant frequency, and determining a property of the fluid constituent on the basis of the corrected resonant frequency.

BRIEF DESCRIPTION OF THE DRAWINGS

Exemplary embodiments are described below with reference to the attached drawings. In detail:

FIG. 9 shows a schematic flowchart of a method according to an exemplary embodiment for providing a MEMS sensor;

FIG. 10 shows a schematic flowchart of a further method for providing a MEMS sensor according to an exemplary embodiment;

FIG. 11 shows a schematic flowchart of a further method for providing a MEMS sensor according to an exemplary embodiment; and FIG. 12 shows a schematic flowchart of a method for measuring a fluid constituent of a fluid with a fluid sensor according to an exemplary embodiment.

DETAILED DESCRIPTION OF ILLUSTRATIVE EMBODIMENTS

Figure 1A:
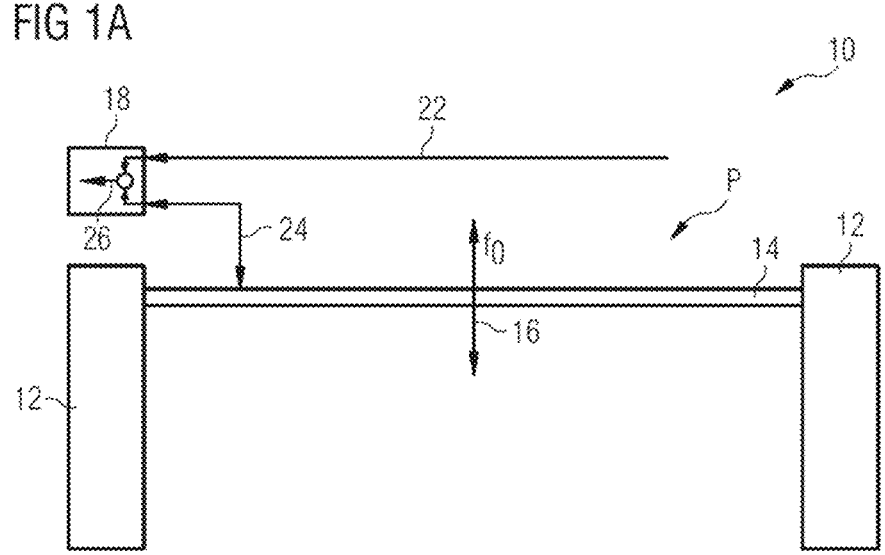
FIG. 1*a* shows a schematic sectional view from the side of a MEMS sensor according to an exemplary embodiment.

Exemplary embodiments develop a MEMS sensor comprising a substrate, a membrane that is suspended from the substrate, the resonant frequency of said membrane being influenced by an ambient pressure that acts on the membrane, and an evaluation device which is configured to perform a measurement that is based on the resonant frequency of the membrane to obtain a measurement result. The evaluation device is embodied to take account of the ambient pressure such that an influence on the measurement result by the ambient pressure is at least partly compensated. This facilitates the at least partial compensation of influences on the sensitivity of the membrane caused by ambient pressure and thus facilitates the reduction or avoidance of measurement errors such that a precise measurement of the fluid or constituents thereof is possible.

Exemplary embodiments develop a MEMS sensor comprising a substrate and a membrane that is suspended from the substrate and an evaluation device which is configured to alternately in time perform a reference measurement based on an unresonant evaluation of a membrane position and perform a measurement based on a resonant frequency of the membrane. By way of example, unresonant measurements can be pressure measurements and/or temperature measurements, in which an electric conductivity and/or a deflection of the membrane is evaluated. A resonant measurement can be an evaluation of the resonant frequency, i.e., the frequency value thereof. This facilitates both precise and space-saving measurements since, firstly, the same membrane is used for different measurements, which is implementable in space-saving manner and this further facilitates possible measurement errors having the same effect on all measurements and possibly being removed by compensation such that precise measurements are obtained.

Exemplary embodiments develop a MEMS sensor comprising a substrate, a membrane that is suspended from the substrate and an evaluation device which is configured to perform a measurement using a deflection of the membrane. The evaluation device is embodied to perform a first implementation of the measurement with a first membrane sensitivity of the membrane and a second implementation of the measurement with a second membrane sensitivity of the membrane and a second implementation of the measurement with a second membrane sensitivity of the membrane or of a further membrane to obtain a combined result by combining a result of the first implementation and a result of the second implementation. This facilitates precise measurement results by a differential combination-type result.

The present disclosure further relates to a pressure-temperature gas combination sensor, which is based on pressure capture, however, embodiments of the present invention can also be applied to other types of sensors. In some embodiments, MEMS sensors advantagously facilitate a determination of a fluid and/or a constituent thereof.

Before exemplary embodiments are explained in more detail below on the basis of the drawings, reference is made to the fact that identical or functionally identical elements, objects and/or structures or elements, objects and/or structures with the same effect are provided with the same reference signs in the different figures, and so the description of these elements presented in the different exemplary embodiments can be interchanged among the various cases and/or be applied to the various cases.

Exemplary embodiments below relate to micro-electromechanical systems (MEMS), in particular MEMS sensors.

Further, exemplary embodiments relate to MEMS sensors for fluidic measurements, i.e., sensors for capturing at least one constituent of a fluid, for instance a liquid or gas. To this end, exemplary embodiments described herein have a membrane which can have a sensitivity. For the purposes of capturing or determining a property of the fluid and/or a constituent thereof, the membrane can be configured to support or provide adsorption of the fluid or a constituent thereof at the surface, which facilitates fluidic contact with the fluid. On the basis of the adsorption, a change of a resonant frequency of the membrane can be obtained, the latter being determinable. On the basis of the knowledge of which fluids and/or constituents are able to be adsorbed by the membrane, a type and/or amount of adsorbed material can be deduced, which is transferable to presence and/or concentration of the fluid.

On the basis of a measurement of the resonant frequency and a deduction of how the change in the resonant frequency correlates with the fluid, exemplary embodiments facilitate an at least partial compensation of cross influences, which are likewise able to change the resonant frequency of the membrane but which are of little importance or no importance for measuring the fluid. By way of example, these include an ambient pressure and/or a temperature, which acts on the membrane. Such parameters may lead to a change in the resonant frequency, to be precise independently of whether the fluid to be captured or constituents thereof are in contact with the membrane. Exemplary embodiments relate to taking account of the influences of the ambient pressure and, optionally, the temperature on the resonant frequency change in order to obtain an exact measurement result.

FIG. 1a shows a schematic sectional view from the side of a MEMS sensor 10 according to an exemplary embodiment. The MEMS sensor 10 comprises a substrate 12 and a membrane 14 that is suspended from the substrate or arranged at the substrate. The membrane 14 is suspended from the substrate 12 in such a way that it is able to vibrate along a vibration direction 16. Vibrations can be understood in such a way that, in addition to static deflection, a dynamic deflection is possible, too, in particular those deflections that vibrate at a resonant frequency. By way of example, this can be the first mode, the second mode or a higher-valued mode. A resonant frequency of a vibration of the membrane 14 along the vibration direction may be influenced by a material stiffness, a Young's modulus and/or a mechanical tension which the substrate 12 provides in respect of the membrane 14. Thus, relatively strong tensile forces of the substrate 12 in respect of the membrane 14 and/or higher material stiffnesses of a material of the membrane 14, for instance silicon, silicon oxide and/or silicon nitride, may bring about an increase in the resonant frequency.

The resonant frequency $f_0$ may be influenced by an ambient pressure P, which acts on the membrane 14. Ambient pressure means a pressure that acts on the membrane 14 in relation to a reference pressure. Thus, an increase in the pressure P in relation to a reference state may lead to a higher force acting on the membrane 14, which may lead to a tensile load in the membrane 14, which can also be understood to be a virtual increase in stiffness. A virtual increase in stiffness with the increasing pressure P can, on the basis thereof, lead to an increase in the resonant frequency $f_0$.

The MEMS sensor 10 comprises an evaluation device 18, which is configured to perform a measurement based on the resonant frequency $f_0$ of the membrane 14 in order to obtain a measurement result. By way of example, the measurement result can be the resonant frequency $f_0$, the frequency value of which is determined. As an alternative or in addition thereto, the measurement result can be an information item which from is derived the resonant frequency, for example a scope Δf of a frequency shift between the determined resonant frequency and a reference state or the like. To this end, the evaluation device 18 can be configured to excite the membrane 14 to vibrate, for instance using a sweep and/or a broadband excitation, for example in a pulse-like manner, and/or using a plurality of narrowband excitations, either simultaneously or alternately in time.

The evaluation device 18 can be embodied to take account of the ambient pressure P such that influencing of the measurement result by the ambient pressure P is at least partly compensated. To this end, the evaluation device 18 can receive a signal 22 that has an information item in respect of the pressure P. The information item can be the pressure P, for example as an absolute value and/or a value related to a relative pressure. As an alternative or in addition thereto, the signal 22 can be a preprocessed information item, for example specifying the scope with which a frequency shift as a result of the ambient pressure P acts in the membrane 14, for example in the form of a frequency value. The influences of the ambient pressure can be stored in the evaluation device 18, and so the latter has knowledge of, for example, what pressure or what value of a pressure leads to what change of the property of the membrane 14. This can be implemented by way of a measurement in advance or a simulation and can be stored, e.g. in a memory which is accessible to the evaluation device 18. As an alternative, the evaluation device 18 can also be supplied directly with information items that relate to the effects in the membrane 14, for example a resonant frequency offset obtained by the pressure P.

Further, the evaluation device 18 can be embodied to obtain a signal 24 having an information item about a deflection and/or a vibration of the membrane 14. By combining the information items in the signal 24 and in the signal 22, it is possible to obtain a corrected measurement result 26, in which an influence of the result in respect of the resonant frequency shift by the ambient pressure P is compensated in part or in full.

The ambient pressure P can be an ambient parameter that changes comparatively slowly. Therefore, it may be sufficient to obtain the signal 22 at time intervals of for example one hour, 15 minutes, one minute, 30 seconds or even shorter intervals. The signal 22 also can be obtained by a measurement carried out by the evaluation device 18 for determining the ambient pressure P. The measurement can be implementable at the same time as, earlier in time than or later in time than the measurement for obtaining the signal 24. As described in detail below, the membrane 14, too, can be used for measuring the ambient pressure P. Expressed differently, the evaluation device 18 is configured to undertake a calibration in respect of the ambient pressure P. To this end, the membrane 14 for determining the ambient pressure P can be used, and so a self-calibration by way of dedicated means is implementable.

Figure 1B:
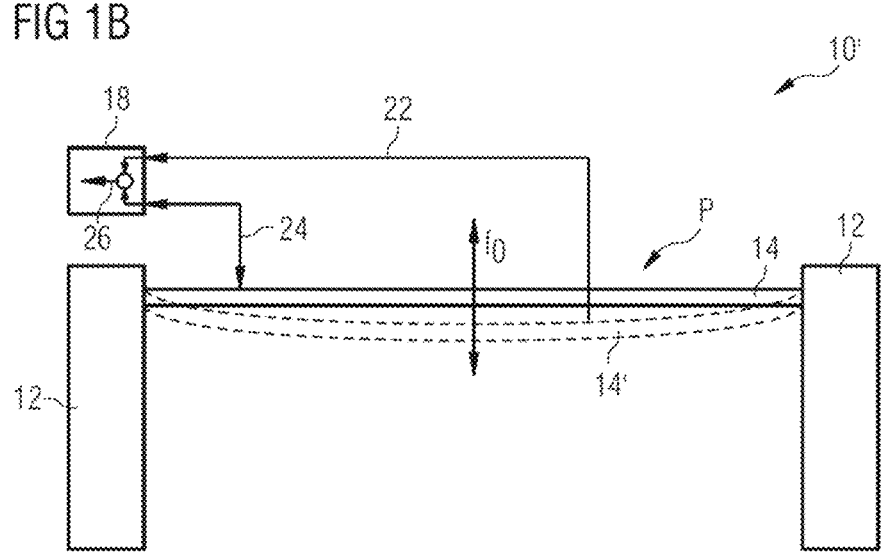
FIG. 1*b* shows a schematic sectional view from the side of a MEMS sensor according to an exemplary embodiment, in which the evaluation device is configured to perform a reference measurement before or after the measurement in time.

FIG. 1b shows a schematic sectional view from the side of a MEMS sensor 10', in which, in order to obtain the signal 22, the evaluation device 18 is configured to perform a reference measurement temporally before or after the measurement for obtaining the signal 24. The ambient pressure P that acts on the membrane 14 may be determinable by means of the reference measurement. The signal 22 can be provided to the evaluation device 18, and so the latter can take account of the acting ambient pressure P for the measurement result 26.

For the purposes of determining the ambient pressure P, the evaluation device 18 can be configured to determine a deflection 14' of the membrane 14. This may provide an indication as to how much the pressure P has changed in relation to a reference pressure, for instance during production of the MEMS sensor 10'. According to an exemplary embodiment, the MEMS sensor 10' can be embodied as a pressure sensor or at least it can have a corresponding functionality. This means that a changeable ambient pressure may lead to a changeable deflection 14' of the membrane 14 and that the evaluation device 18 can be configured to determine the deflection 14' and to correlate the latter to an acting ambient pressure P or a frequency shift in the resonant frequency $f_0$ obtained by the deflection.

Expressed differently, the MEMS sensor 10' can perform a reference measurement alternately in time, said reference measurement being based on an unresonant evaluation of a membrane position of the membrane 14. Alternately thereto, the MEMS sensor 10' can perform the measurement for obtaining the signal 24. For the purposes of evaluating the deflection 14', use can be made of an unresonant evaluation of the membrane position; this means that it is possible to dispense with a resonant excitation of the membrane 14. In addition to determining the ambient pressure P, the evaluation device 18 can also determine a temperature T acting on the membrane 14.

The evaluation device 18 can be embodied to use the determined ambient pressure P or the effect on the membrane 14 derived therefrom to perform a calibration in respect of the measurement 24. By way of example, the influence determined at distances or intervals can be saved or stored and used for correcting the results in the signal 24 until the ambient pressure P is captured again.

In addition to a temperature and/or pressure, a natural frequency or a resonant frequency of the membrane 14 may also be influenced by an electric bias voltage, which is applied to the membrane 14. This electric bias voltage can induce a force into the membrane 14, said force also influencing the resonant frequency $f_0$. The evaluation device 18 can be embodied to change the electric bias voltage on the basis of the signal 22 in order to take account of the ambient pressure. This means that a falsification of the measurement result 26, caused by the ambient pressure P and, possibly, the temperature T, can be compensated by a compensation, in advance, in the electric bias voltage of the membrane 14.

Figure 2:
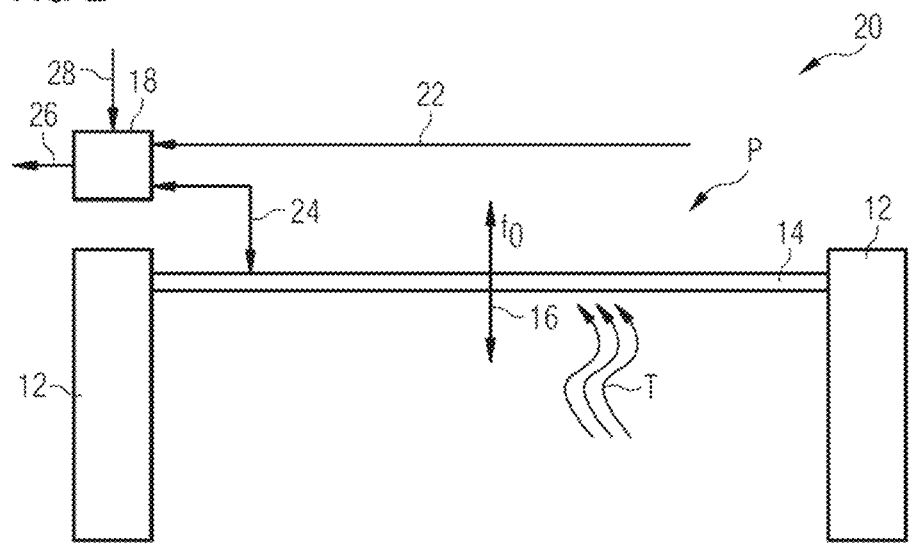
FIG. 2 shows a schematic sectional view from the side of a MEMS sensor according to an exemplary embodiment, said MEMS sensor being configured to take account of an ambient temperature.

FIG. 2 shows a schematic sectional view from the side of a MEMS sensor 20 according to an exemplary embodiment that has the functionality of the MEMS sensor 10. The evaluation device 18 is configured to obtain the signal 22 with information items in respect of the ambient pressure P and a signal 28, which has an information item in respect of an ambient temperature T acting on the membrane 14. In relation to a reference temperature, warming up or a temperature increase can lead to a stiffness in the material of the membrane 14 reducing, and so a reduction in the resonant frequency $f_0$ may be obtained. Conversely, cooling down may lead to an increase in the resonant frequency $f_0$. The evaluation device 18 can be embodied to use both an information item in respect of the ambient temperature T and also in respect of the ambient pressure P in order to obtain the corrected measurement result 26.

The evaluation device 18 can be embodied to obtain the signal 28 from a temperature sensor. By way of example, the signal 28 can comprise an information item about the temperature prevalent at the membrane or in the membrane 14, a temperature difference in respect of a reference temperature and/or an influence on the resonant frequency $f_0$ caused by the temperature T. This means that the evaluation device 18 can be configured to take account of the ambient pressure P and the ambient temperature T, and so an influence on the measurement result 26 by the ambient pressure P and the ambient temperature T is at least partly compensated.

Figure 3:
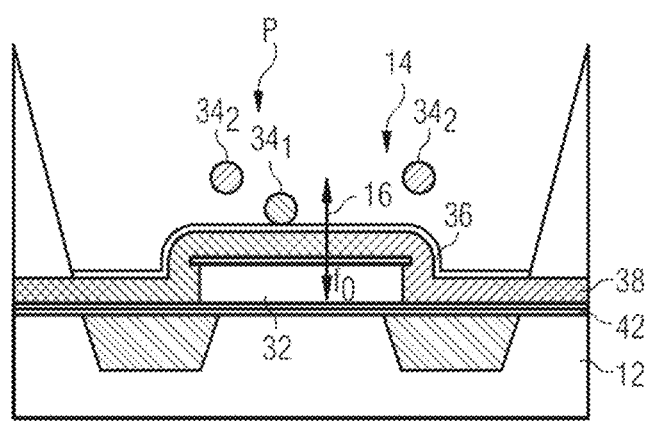
FIG. 3 shows a schematic sectional view from the side of a membrane according to an exemplary embodiment, as is usable in MEMS sensors as described herein.

FIG. 3 shows a schematic sectional view from the side of the membrane 14, as is usable in MEMS sensors described herein. In relation to the substrate 12, the membrane 14 can have a reference volume 32, which is predominantly or completely closed off such that a variation in the ambient pressure P can lead to a variable deflection of the membrane 14. As an alternative or in addition thereto, the membrane 14 can be configured to facilitate an adsorption of a fluid constituent $34_1$. A fluid can have a plurality of different fluid constituents $34_1$ and/or $34_2$ and/or further constituents. The membrane 14 can be embodied to admit an adsorption of a first constituent $34_1$ to a greater extent than the adsorption of a second constituent $34_2$. By way of example, a material of the membrane 14, which is connected to the fluid, may have a corresponding selectivity. To this end, the membrane itself or a coating 36 of same may have a corresponding property. By way of example, silicon nitride (SiN) is a material that can be used for the membrane 14 in order to prevent a short circuit of an electrode 38 of the membrane 14 if mechanical contact with other elements occurs. At the same time, SiN may be configured to adsorb hydrogen and/or water. Other materials likewise can be used as a material of the membrane 14 and/or of a coating 36 and can have other adsorption properties. On the basis of the adsorption of the component $34_1$, a change in mass of the membrane 14 can be obtained, which may lead to a shift in the natural frequency since the vibration response of the membrane 14 is changed. On the basis of the knowledge for which of the constituents $34_1$ and $34_2$ of the fluid the membrane 14 has adsorbing properties, a mass adsorbed at the membrane 14 can be deduced with knowledge of the resonant frequency shift and, consequently, it is possible to deduce a number of molecules and/or a component and, consequently, a concentration of the constituent $34_1$ in the fluid.

The evaluation device can be embodied to resonantly excite the membrane 14, for instance using an electrode 38 of the membrane 14 and a reference electrode 42, which may be securely connected to the substrate 12, for example. On the basis thereof, the evaluation device can be embodied to obtain an information item in respect of the ambient fluid or the adsorbed component $34_1$.

Expressed differently, MEMS sensors according to exemplary embodiments can exploit a so-called μ-balance principle. By way of example, humidity may be adsorbed on nitride, for instance at a membrane of a pressure sensor. This can lead to an increased membrane mass and hence to a decreasing resonant frequency.

Sensitivity of the membrane can be described on the basis of the rule $$S = \frac{\Delta f}{\Delta m} \sim \frac{f_0}{m_0}$$

where S is the sensitivity of the membrane, $\Delta f$ is the shift in the resonant frequency, $\Delta m$ is the change in mass and mo is the reference mass.

Pressure sensors can be suitable for use both as a pressure sensor and as fluid sensors as they have a low membrane mass, i.e., already small changes lead to clear measurement signals. Further, the membranes have high resonant frequencies and can be formed in such a way that a distance between the membrane and a reference electrode, for instance the electrode 42, can be small such that an efficient deflection of the membrane can already be obtained at low electric voltages. The MEMS sensors according to exemplary embodiments can be manufactured using the same technology as pressure sensors and/or temperature sensors. Here, different and independent information items can be used to reduce or exclude a cross influence of temperature and/or pressure.

In exemplary embodiments, a concept of a capacitive pressure sensor can be used and can be extended by an additional resonant readout mode, by means of which, for example, it is possible to evaluate a sensitivity in respect of a fluid and obtain the functionality of a fluid sensor. The pressure can be measured by way of a capacitive readout, which can be comparatively insensitive in relation to humidity and/or gases and/or fluids. This means that the pressure information item can be present independently of the fluid information item. The temperature can likewise be measured on the chip, i.e., in the sensor, for example as a constituent of a readout circuit, for instance of an application-specific integrated circuit (ASIC). Information items in respect of the pressure and/or the temperature can be used to remove cross influences in the resonant mode by calculation in order to extract a shift of the resonant frequency as a result of humidity and/or fluid constituents.

Figure 4A:
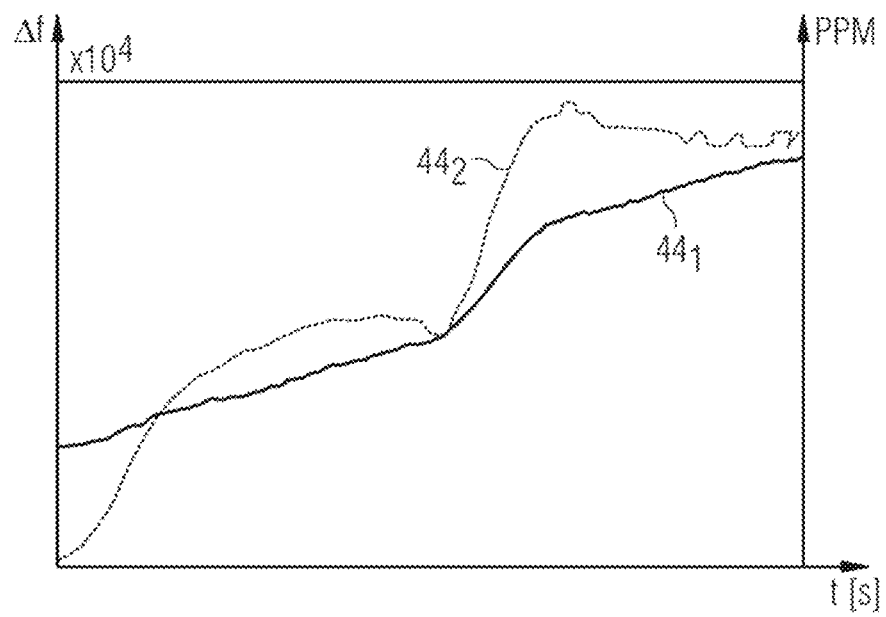
FIG. 4*a* shows a graph, in which the time axis is illustrated on the abscissa and an obtained frequency shift is illustrated on an ordinate.
Figure 4B:
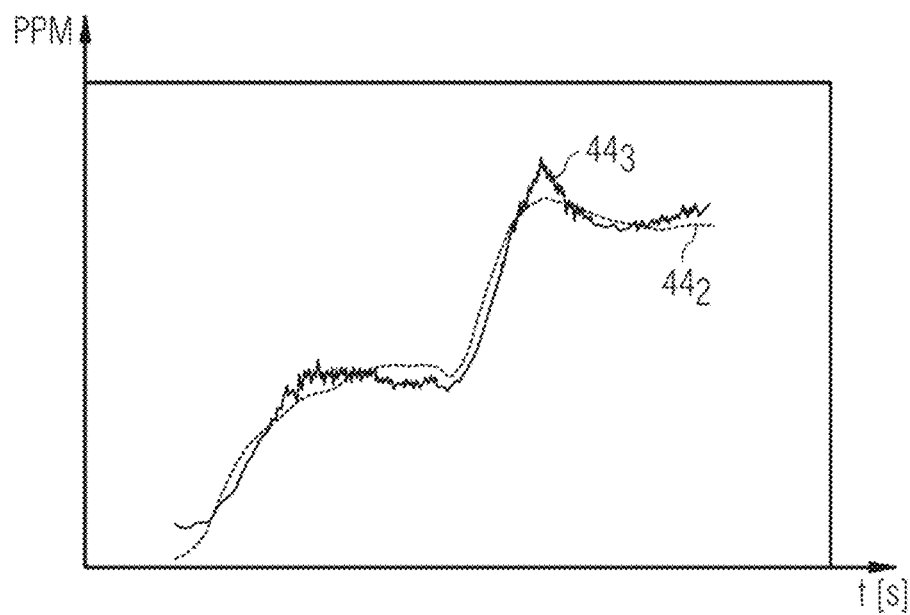
FIG. 4*b* shows a schematic illustration of an inverse model of the graph from FIG. 4*a* on the same time axis.

FIGS. 4a and 4b schematically show a relationship between a changeable temperature influence and a changeable measurement of a concentration PPM (parts per million) of a constituent of a fluid.

Here, FIG. 4a shows the time axis on the abscissa and an obtained frequency shift Δf at an ordinate. Here, a first curve $44_1$ shows raw data of the obtained frequency shift Δf over time. A curve $44_2$ shows a concentration PPM of a material, for instance humidity or water, at a further ordinate over the time axis t in a non-adapted state.

FIG. 4b shows a schematic illustration of both curves after applying an adaptation function, by means of which a temperature and pressure compensation can be obtained. In respect of an adaptation of the temperature, the adaptation function can be based on a calculation rule according to:

$$\Delta f = a_0 + a_1 * PPM + a_2 * T + a_3 * (PPM * T)$$

By way of example, in a nonrestrictive example, −6904.6 Hz can be used as value $a_0$, i.e., $a_0$ denotes a coefficient with units of frequency. The value of 5.500216 Hz/PPM can be used as coefficient $a_1$, i.e., $a_1$ denotes a coefficient with units of frequency depending on the concentration. By way of example, −229.733 Hz/° C. can be used as value for the coefficient $a_2$, i.e., $a_2$ is a coefficient with units of frequency depending on the ambient temperature. By way of example, a value of −0.11024 Hz/(PPM*° C.) can be used as value for the coefficient $a_3$, i.e., $a_3$ can denote a coefficient with units of frequency depending on a combination of the concentration and the ambient temperature. Building hereon, the concentration can be calibrated as follows:

$$PPM = (\Delta f - a_0 - a_2 * T)/(a_1 + a_3 * T)$$

Here, FIG. 4b shows a curve $44_3$ which displays the adapted measurement values $44_1$ from FIG. 4a. Further, the curve $44_2$ of FIG. 4a is displayed. By way of example, the pressure compensation can be implemented on the basis of the calculation rule $$\Delta f(P, T, PPM) = \sum_{i=0}^{n} \sum_{j=0}^{n} \sum_{k=0}^{n} a_{i,j,k} P^i T^j PPM^k$$

which can be implemented by the solution or reformulation according to

Solve $\Delta f(P,T,PPM)$ polynomial for $PPM \rightarrow PPM(P,T,\Delta f)$

Consequently, the value for the concentration PPM can be obtained by resolving the polynomial for PPM. The evaluation device can have stored an appropriate formulation or it can determine and apply the latter itself. Here, the variable P denotes the pressure, the variable T denotes the temperature and PPM denotes the concentration. $a_{i,j,k}$ describe coefficients which, as explained for the coefficients $a_0$, $a_1$, $a_2$ and $a_3$, yield a frequency value in combination with the respective parameters P, T and/or PPM. In general, the adaptation function or calibration function can be representable as a polynomial the n-th order.

The equations above can be complemented by interaction terms, i.e., terms which are proportional to a combination of at least two parameters of pressure P, concentration PPM and temperature T, for instance P*T or P*PPM. In general, it is possible to implement a regression in respect of all known measured variables up to the n-th order in order to calibrate the sensor. The pressure P can be captured and thus be taken account of in the embodiments. The PPM-dependence has a positive coefficient within the figures, which can contradict an expectation of a frequency reducing when the membrane becomes heavier. However, the graphs also exhibit a sign-inverted $-\Delta F$ in place of a $\Delta F$, as a result of which an increase in concentration also leads to an increase of this negatively defined parameter.

The MEMS sensor 20 can be embodied to provide a measurement signal, for instance the signal 26, which has an information item in respect of the ambient pressure P, the ambient temperature T and in respect of a fluid that interacts with the membrane 14, on the basis of the reference measurement for determining the ambient pressure P and on the basis of the measurement. This means that the information items that can be used for rectifying or correcting the measurement result can also be output, for example to be presented to a user. The information items in respect of the fluid can be an information item in respect of a constituent of the fluid and/or a concentration of the fluid or of a constituent thereof.

It is understood that the illustrated values are purely of exemplary nature, just like the illustrated function. Other functions and/or values can be used for as long as these sufficiently accurately map the dependencies of the measurement results in respect of the fluid constituent on the cross influences, for instance temperature, pressure and/or electric bias voltage. The values illustrated here serve only illustrative purposes.

Expressed differently, there is great demand for integrated environmental sensors for building automation and also for consumer appliances such as, for instance, smartphones. Measurement parameters to be highlighted in this case are, for example, a temperature, a pressure and/or an air humidity. However, other gases, such as, for instance, carbon dioxide ($CO_2$) or volatile organic compounds (VOC), are increasingly of interest. Such measurements can be captured by means of MEMS sensors according to exemplary embodiments and corresponding measurement data can be output. To this end, exemplary embodiments use membrane structures, as these are usable both for a pressure measurement and for resonant measurements of air humidity and/or gas sensors. Such a concept facilitates a monolithic integration of a humidity or gas sensor with temperature and/or pressure sensors on the same platform in terms of technology. As a result, an information item of the capacitive pressure measurement and the resistive temperature measurement and the readout circuits thereof are used in order to at least partly compensate the cross influence or cross sensitivity of the resonant humidity signal or gas signal. In this respect, exemplary embodiments relate to a combined sensor/combination sensor for measuring pressure, temperature, humidity and/or other gases, which can be formed and manufactured as an integrated capacitive pressure sensor. Particularly in the field of measuring humidity, the MEMS membranes can facilitate an avoidance or reduction of material degradation in relation to coated polymer films, as are used for comb capacitors, for example. Further, it is possible to obtain long service lives and short response times.

Exemplary embodiments use a membrane-based pressure sensor and a temperature sensor, which can both be evaluated using a non-resonant readout method, and add an additional mode of operation to this concept, in which the resonant frequency of the membrane is used to measure a fluid property such as humidity, gas concentrations or the like, wherein the concept of the resonant μ-balance can be used to this end, where humidity and/or other gases are adsorbed at the membrane and consequently reduce the resonant frequency thereof. In detail:

1. The membrane can be similar or equal to membranes that are used for pressure measurements; i.e., it is possible to dispense with technological outlay for modifying the MEMS membrane, the additional functionality can be obtained in a surface-neutral manner;
2. Since the resonance of the μ-balance is sensitive to pressure, temperature and concentration effects (molecular loading), a non-resonant readout concept for pressure and temperature can be used to exclude or extract the concentration effects. Using the determined pressure and the determined temperature and/or information items derived therefrom, it is possible to calibrate the resonant readout circuit and to precisely determine the concentration, i.e., the humidity concentration or the gas concentration or the liquid concentration;
3. The response time of the MEMS sensor can be short and can be partly or completely independent of slow diffusion processes into the material, as may occur in polyimide or other polymers. Further, MEMS sensors according to exemplary embodiments can be independent of a condensation; i.e., it is possible to dispense with an arrangement of a heater or heating element for heating the membrane. Such a heating element can be embodied to reverse a diffusion of a constituent of a fluid into the membrane. As a result of the lower relevance of the diffusion into the membrane in present exemplary embodiments, it is possible to dispense with an arrangement of such heating elements. This facilitates a lower power uptake of the MEMS sensor and further facilitates the avoidance of thermal noise due to heating of the MEMS sensor, which could end up with the readout circuit of the pressure sensor being influenced.

As an alternative or in addition to the calibration of a MEMS sensor for a resonant measurement by using the ambient pressure, it is possible also to describe exemplary embodiments, for example the MEMS sensor 10, in such a way that a MEMS sensor has the substrate 12 and the membrane 14 suspended from the substrate 12. The evaluation device 18 can be configured to perform, alternately in time, a reference measurement, which is based on an unresonant evaluation of a membrane position, for example for capturing the pressure P and/or the temperature T. Alternately herewith, it is possible to perform a measurement based on a resonant frequency of the membrane, for instance for determining a fluid constituent.

These exemplary embodiments are combinable with one another as desired; this means that the just described exemplary embodiment can also be configured in such a way that the MEMS sensor is configured to obtain a measurement result on the basis of the measurement in respect of the fluid, wherein the evaluation device 18 can be embodied to determine, on the basis of the reference measurement, an environmental influence, for instance an acting temperature and/or an acting pressure, which acts on the membrane 14. Further, the evaluation device 18 can be embodied to take account of the environmental influence such that an influence on the measurement result 26 by the environmental influence is at least partly compensated.

As an alternative or in addition thereto, the evaluation device 18 can be embodied to provide, on the basis of the reference measurement, an information item in respect of an ambient pressure P, which acts on the membrane 14. The evaluation device 18 can be embodied to take account of the influence of the ambient pressure P on the resonant frequency fo of the membrane during the measurement.

Exemplary embodiments described above allow precise measurements in respect of a fluid constituent and/or other resonant measurements to be obtained by using information items in respect of ambient conditions or environmental influences which can be obtained, for example, by non-resonant measurements. Below, a further option is discussed for obtaining precise measurements.

Here, different membrane sensitivities are used to obtain different measurement results on the basis of a prevalent state, said measurement results being combinable with one another. To this end, a single membrane, for example, can be put into states of different sensitivity in order to obtain the different results. As an alternative or in addition thereto, use can be made of two mutually separate membranes with different sensitivities. By way of example, a variable, for instance a membrane diameter, can contribute to setting a sensitivity of a membrane. Different amounts of fluid constituents can accumulate on membranes of different sizes and/or cause a different change in the mass or resonant frequency. As an alternative or in addition thereto, mutually different sensitivities can be obtained by applying mutually different electric bias voltages.

Figure 5:
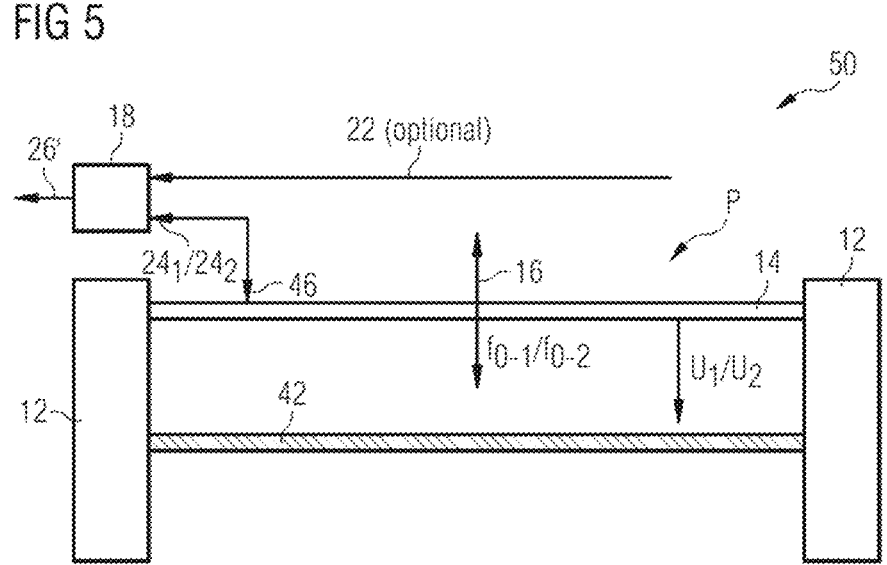
FIG. 5 shows a schematic sectional view from the side of a MEMS sensor according to an exemplary embodiment, said MEMS sensor being configured to apply different electric bias voltages to the membrane.

FIG. 5 shows a schematic sectional view from the side of a MEMS sensor 50 according to an exemplary embodiment. The MEMS sensor 50 comprises the membrane 14 that has been suspended from the substrate 12 and the evaluation device 18, which is configured to perform a measurement using a deflection of the membrane 14, for example a pressure measurement and/or resonant measurement, for instance for evaluating a fluid that is interacting with the membrane 14. The evaluation device 18 is configured to perform a first implementation of such a measurement with a first membrane sensitivity of the membrane 14 and a second implementation of the measurement with a second membrane sensitivity of the membrane 14. The evaluation device 18 is embodied to obtain a combined result 26' by combining a result of the first implementation and a result of the second implementation. To this end, the evaluation device 18 is embodied, for example, to apply mutually different electric bias voltages $U_1$ and $U_2$ for carrying out respectively one measurement and for obtaining corresponding signals $24_1$ and $24_2$. To this end, the evaluation device 18 can be embodied to provide a control signal 46, which applies the electric bias voltage to the membrane 14 or which at least has an information item in this respect. By way of example, the electric bias voltage can be measured in relation to the reference electrode 42. A changeable electric bias voltage is readily implementable in other MEMS sensors as well, for instance in the MEMS sensors 10, 10' or 20.

Optionally, the signal 22 in respect of the pressure P can be taken into account in the measurement result 26, as was explained, for example, in conjunction with the MEMS sensors 10, 10' or 20. Optionally, the MEMS sensor 5o can be configured to take account of the signal 22, i.e., information items in respect of the ambient pressure. As an alternative an addition thereto, the temperature can also be taken into account.

The different electric bias voltages can cause different force decouplings in the membrane 14, which leads to a different effect of a temperature, pressure and/or fluid adsorption on the vibration properties of the membrane, similar to changeable temperatures and/or different pressures and/or various membrane dimensions. By way of example, this can lead to different resonant frequencies $f_{0-1}$ or $f_{0-2}$ being obtained. By combining the results, for instance by forming a mean value or the like, it is possible to at least partly compensate errors, for instance according to differential measurement value formation.

This means that the evaluation device 18 can be embodied to perform a reference measurement for determining the ambient pressure with a first value of the changeable electric bias voltage, for instance $U_1$, in order to obtain a first partial result. The evaluation device 18 can be embodied to perform the measurement again with a second value of the changeable electric bias voltage in order to obtain a second partial result. The MEMS sensor 50 can be embodied to perform differential processing of the first partial result and of the second partial result in order to obtain the measurement result 26. In the case of capacitive pressure sensors, the voltage can be increased up to, at most, the pull-in voltage, at which a mechanical contact may arise between the membrane and a stator. Consequently, any voltage that is smaller than the pull-in voltage can be used as electric bias voltage. In the case of higher voltages, the membrane snaps onto the substrate and, accordingly, can no longer vibrate. This pull-in voltage can be influenced by a gap distance and the stiffness of the membrane (thickness, bias voltage and/or lateral dimensions). Possible, but nonrestrictive, values of a pull-in voltage have a voltage value of at least 10 V and at most 15 V; however, it is also possible to design it into regions up to 100 V by way of adaptations. Exemplary embodiments have an electric bias voltage in a range from 0 V to at most 100 V, of at least 5 V to at most 30 V or of at least 10 V and at most 15 V, for example in a region of approximately 12 V that is relevant to motor vehicles.

Figure 6:
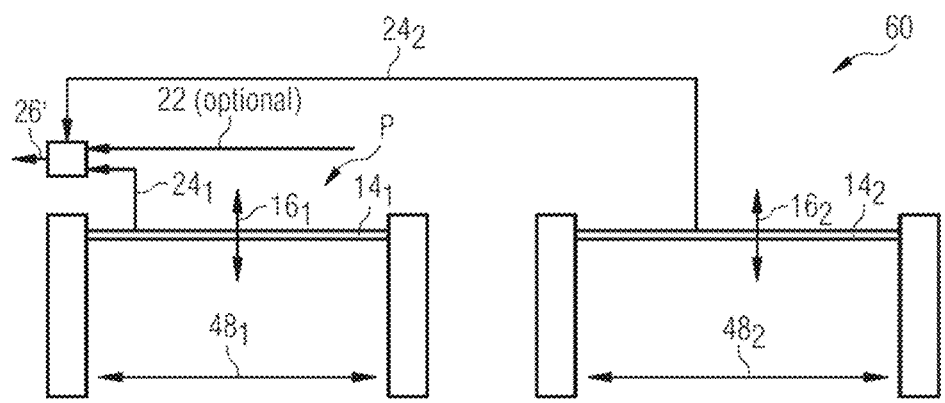
FIG. 6 shows a schematic sectional view from the side of a MEMS sensor according to an exemplary embodiment, said MEMS sensor having a first membrane and a second membrane.

FIG. 6 shows a schematic sectional view from the side of a MEMS sensor 60 according to an exemplary embodiment having a first membrane $14_1$ and a second membrane $14_2$. The membranes $14_1$ and $14_2$ can have sensitivities that differ from one another. To this end, different electric bias voltages may be applicable to the membranes $14_1$ and $14_2$. As an alternative or in addition thereto, the membranes $14_1$ and $14_2$ may have membrane diameters or membrane surfaces 481 and 482 that differ from one another, facilitating sensitivities that differ from one another. This allows the signals $24_1$ and $24_2$ to be obtained at the same time or simultaneously such that the combination-based result 26 is providable within a short period of time.

As already explained, the membranes $14_1$ and $14_2$ can have different sensitivities in respect of a constituent of the fluid. In addition to mutually different diameters $48_1$ and/or $48_2$, different electric bias voltages or the like, it is also possible to use mutually different coatings in order to set a different sensitivity. For the purposes of differential processing of results, the same measurement can be carried out with different membranes $14_1$ and $14_2$ of different sensitivities. If use is made of a changeable parameter, for instance the electric bias voltage, in order to set the changeable sensitivity, it is also possible to use the same membrane and perform a measurement twice, i.e., in a first run-through and in a second run-through. Both concepts, the use of two membranes and the change in the sensitivity of one membrane, can be combinable with one another in order to obtain an increased measure of the measurement results.

As an alternative or in addition thereto, it is likewise possible to configure the membranes 14 and 14 in such a way that the membranes 14 and 14 are configured for an adsorption of different constituents of a fluid in order to obtain measurement results in respect of different constituents.

For the sensitivities described herein, it is possible that one of the sensitivities has a greater value than the other sensitivity. If a quotient is formed, in which, for example, the sensitivity with the greater value is in the numerator and the sensitivity with the smaller value is in the denominator, the quotient can have a value of at least 1.01 and at most 10, at least 1.05 and at most 3, or at least 1.08 and at most 2, for instance 1.1.

Expressed differently, in addition to the temperature and the pressure, a cross sensitivity can also be obtained by an electric bias voltage, which may be a DC voltage. In order to facilitate a differential evaluation, membranes of different sensitivity can be used and/or a bias voltage can be changed so as to change the resonant frequency and hence the sensitivity. Therefore, the measurement principles explained above can be expanded as follows:

4. Using differently functionalized membranes in order to expand the approach in the direction of an integrated multi-gas pressure-temperature combination sensor.
5. The DC voltage of the sensor can be used to shift the resonant frequency fo and hence the sensitivity of the sensor, which is also describable by the relationship between the shift Δf of the resonant frequency depending on the change in mass Δm:

$$S = \frac{\Delta f}{\Delta m} \sim f_0(V_{DC})$$

where $V_{DC}$ is the bias voltage of the sensor.
6. By changing or switching the bias voltage, it may thus be possible to realize different readout principles without arranging a reference cell, facilitating a low spatial requirement. Furthermore, it is possible to compensate creeping changes (drifts) in the sensor.

The exemplary embodiments can be manufactured using the same technology as pressure sensors, facilitating the maintenance of a technical level of complexity. Although additional outlay may occur in respect of a functionalization of a membrane in respect of gases or fluids, this however is combined with a gain in functionality. For sensing air humidity, it is possible to use already used SiN layers. Pressure sensor membranes can be used directly for the resonance evaluation; consequently, the MEMS component can be embodied in a surface-neutral fashion. Nevertheless, a monolithic multi-gas sensor can be arranged for further functionalizations of membranes. Here, use can also be made of heaters, even though these are not mandatory. The sensors can provide pressure, temperature and/or information items about the fluid as a combination sensor. The concept of the bias voltage circuit allows the requirement of a stable and/or adapted reference cell to be avoided and may even have advantages in this respect in relation to eliminating drift. The use of integrated pressure sensor membranes as resonant humidity sensors or gas sensors, wherein the pressure and the temperature are used for correcting the cross sensitivities and wherein is implemented in a non-resonant manner and this is consequently insensitive to humidity and/or gas, is one aspect of the exemplary embodiments described herein. The electric bias voltage of the resonant sensor can be used to adapt its sensitivity. This facilitates a differential readout without the requirement of a separate, insensitive reference cell. Exemplary embodiments use the electric bias voltage to actively change the resonant frequency of the membrane and hence the sensitivity thereof.

Figures 7, 8:
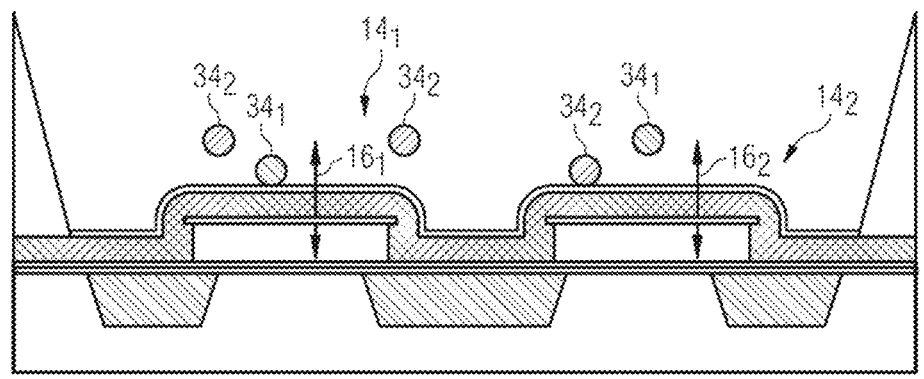
FIG. 7 shows a schematic sectional view from the side of a membrane arrangement according to an exemplary embodiment, comprising a first membrane and a second membrane which have different functionalizations.
FIG. 8 shows a schematic table having four different types of membranes according to an exemplary embodiment, said membrane types differ in respect of their membrane sizes.

FIG. 7 shows a schematic sectional view from the side of a membrane arrangement comprising a first membrane $14_1$ and a second membrane $14_2$, which are functionalized differently and which have different adsorption properties in respect of different fluid constituents $34_1$ and $34_2$. The membrane $14_1$ can be configured to admit an adsorption of the fluid constituent $34_1$ to a greater extent in comparison with the fluid constituent $34_2$ or to admit no adsorption in respect of the fluid constituent $34_2$. In this respect, the membrane $14_2$ can have an inverted configuration and tend to facilitate an adsorption of the fluid constituent $34_2$ rather than the fluid constituent $34_1$.

FIG. 8 is a schematic table with four different types of membrane that differ in terms of their membrane sizes; otherwise, they have the same properties, in particular in respect of thickness and employed material. Types 1 and 2 have a single membrane size with a diameter of 13.2 μm. By contrast, type 3 has increased dimensions with a membrane size of 20 μm, whereas type 4 has a membrane size of 12.6 μm, which is reduced in relation to types 1 and 2. A resonant frequency $f_0$, specified in megahertz in an exemplary manner, has a value of approximately 31 to 32 MHz for types 1 and 2. The comparatively larger membrane of type 3 has a reduced natural frequency in the region of approximately 17 MHz and the membrane of type 4, which is comparatively smaller, has a resonant frequency which, at 34 MHz, is increased. From this, it is clear that membranes with different dimensions may have different sensitivities.

FIG. 9 shows a schematic flowchart of a method 1000 for providing a MEMS sensor, for instance the MEMS sensor 10, 10', 20 or another MEMS sensor. The method includes a step 1100 for providing a substrate. In a step 1200, a membrane is suspended from the substrate such that the resonant frequency of said membrane is influenced by an ambient pressure. A step 1300 includes arranging an evaluation device such that the latter is configured to perform a measurement that is based on the resonant frequency of the membrane in order to obtain a measurement result, such that the evaluation device is embodied to take account of the ambient pressure such that an influence on the measurement result by the ambient pressure is at least partly compensated.

FIG. 10 shows a schematic flowchart of a method 2000 for providing a MEMS sensor, for example the MEMS sensor 10', 50 or 60. In a step 2100, a substrate is provided. In a step 2200, a membrane is suspended from the substrate. In a step 2300, an evaluation device is arranged such that the latter is configured to alternately in time perform a reference measurement based on an unresonant evaluation of a membrane position and perform a measurement based on a resonant frequency of the membrane.

FIG. 11 shows a schematic flowchart of a method 3000 for providing a MEMS sensor, for instance the MEMS sensors 50 and/or 60. The method includes providing a substrate in a step 3100. In a step 3200, a membrane is suspended from the substrate. In a step 3300, an evaluation device is arranged such that the latter is configured to perform a measurement using a deflection of the membrane. In a step 3400 the evaluation device is configured such that the latter is configured to perform a first implementation of the measurement with a first membrane sensitivity of the membrane and a second implementation of the measurement with a second membrane sensitivity of the membrane or of a further membrane and to obtain a combined result by combining a result of the first implementation and a result of the second implementation.

FIG. 12 shows a schematic flowchart of a method 4000 for measuring a fluid constituent of a fluid with a fluid sensor, for instance a MEMS sensor 10, 10', 20, 50 or 60 used as a fluid sensor. The sensor can have a membrane 14 that is suspended from the substrate 12. In a step 4100, the membrane is contacted with a fluid such that the membrane adsorbs a fluid constituent. In a step 4200, a resonant frequency of the membrane is captured. In a step 4300, an ambient pressure on the resonant frequency is taken account of in order to obtain a corrected resonant frequency. In a step 4400, a property of the fluid constituent is determined on the basis of the corrected resonant frequency.

Reference is made to the fact that the description and numbering used herein leaves the sequence of the steps open. Thus, for example, taking account of the ambient pressure in step 4300 during the method 4000 may also take place before contacting the membrane in step 4100 and/or before capturing a resonant frequency in step 4200.

Additional exemplary embodiments and aspects of the invention, which can be used individually or in combination with the features and functionalities described herein, are described.

According to a first aspect, a MEMS sensor 10; 10'; 20 can have the following features: a substrate 12; a membrane 14 that is suspended from the substrate 12, the resonant frequency fo of said membrane being influenced by an ambient pressure P that acts on the membrane 14; and an evaluation device 18 which is configured to perform a measurement that is based on the resonant frequency $f_0$ of the membrane 14 in order to obtain a measurement result 26; and wherein the evaluation device 18 can be embodied to take account of the ambient pressure P such that an influence on the measurement result 26 by the ambient pressure P is at least partly compensated.

According to a second aspect when referring back to the first aspect, the evaluation device can be configured to take account of the ambient pressure P and an ambient temperature T that acts on the membrane 14 such that an influence on the measurement result 26 by the ambient pressure P and the ambient temperature T is at least partly compensated.

According to a third aspect when referring back to the first aspect, the MEMS sensor can be configured to perform a reference measurement before or after the measurement in time in order to determine the ambient pressure P that acts on the membrane 14 and in order to provide a result of the reference measurement of the evaluation device 18.

According to a fourth aspect when referring back to the first aspect, the evaluation device 18 can be configured to determine the ambient pressure P on the basis of a deflection 14' of the membrane 14.

According to a fifth aspect when referring back to the first aspect, the MEMS sensor can be configured to alternately in time perform a reference measurement based on an unresonant evaluation of a membrane position and perform the measurement.

According to a sixth aspect when referring back to the fifth aspect, the evaluation device 18 can be embodied to use a result of the reference measurement to determine the ambient pressure P and to perform a calibration in respect of the measurement.

According to a seventh aspect when referring back to the first aspect, the measurement result 26 can depend on an ambient fluid $34_1$, $34_2$, which interacts with the membrane 14, wherein the evaluation device 18 can be embodied to resonantly excite the membrane 14 to obtain an information item in respect of the ambient fluid $34_1$, $34_2$.

According to an eighth aspect when referring back to the first aspect, the evaluation device 18 can be embodied to take account of a concentration of a constituent $34_1$, $34_2$ of a fluid that interacts with the membrane 14 on the basis of the rule $$PPM=(\Delta f-a_0-a_2*T)/(a_1+a_3*T)$$

where $\Delta f$ denotes a shift of the resonant frequency fo of the membrane 14 obtained by the influence of the ambient temperature T and the ambient pressure P, $a_0$ denotes a frequency, $a_1$ denotes a frequency depending on the concentration, $a_2$ denotes a frequency depending on the ambient temperature T, $a_3$ denotes a frequency depending on the concentration multiplied by the ambient temperature T, $a_1$ denotes the ambient pressure P, $a_2$ denotes the ambient temperature T and $a_3$ denotes a frequency depending on a combination of the concentration with the ambient temperature T.

According to a ninth aspect when referring back to the first aspect, the MEMS sensor can be configured to provide a measurement signal 26 on the basis of a reference measurement for determining the ambient pressure P and on the basis of the measurement, said measurement signal having an information item in respect of the ambient pressure P, an ambient temperature T and a fluid that interacts with the membrane 14.

According to a tenth aspect when referring back to the first aspect, the membrane 14 can be embodied to facilitate adsorption of a constituent $34_1$, $34_2$ of a fluid at the membrane 14, wherein the adsorption of the constituent $34_1$, $34_2$ can cause a change in the mass of the membrane 14 bringing about a resonance shift of a natural frequency $f_0$ of the membrane 14, wherein the evaluation device 18 can be configured to output a measurement signal 26 that has an information item in respect of the resonance shift.

According to an eleventh aspect when referring back to the tenth aspect, the membrane 14 can be a first membrane $14_2$ and the sensor can have at least one second membrane $14_1$, wherein the first and second membrane $14_1$, $14_2$ are configured for an adsorption of different constituents $34_1$, $34_2$ of the fluid.

According to a twelfth aspect when referring back to the first aspect, the MEMS sensor can be formed in absence of a heating element for heating the membrane 14 to reverse diffusion of a constituent of a fluid into the membrane 14.

According to a thirteenth aspect when referring back to the first aspect, the evaluation device 18 can be embodied to apply a changeable electric bias voltage $U_1$, $U_2$ to the membrane 14 in order to set a changeable natural frequency of the membrane 14.

According to a fourteenth aspect when referring back to the thirteenth aspect, the evaluation device 18 can be embodied to change the changeable electric bias voltage $U_1$, $U_2$ on the basis of a result of the measurement.

According to a fifteenth aspect when referring back to the thirteenth aspect, the evaluation device 18 can be embodied to perform a reference measurement for determining the ambient pressure P at a first value of the changeable electric bias voltage $U_1$ in order to obtain a first partial result and perform the measurement again with a second value of the changeable electric bias voltage $U_2$ in order to obtain a second partial result, wherein the MEMS sensor is embodied to perform differential processing of the first partial result and of the second partial result in order to obtain a result of the second measurement.

According to a sixteenth aspect when referring back to the first aspect, the membrane 14 can be a first membrane 14 which has a first sensitivity in respect of a constituent of a fluid, wherein the MEMS sensor further can have a second membrane 14 which has a second sensitivity in respect of the constituent of the fluid; wherein the MEMS sensor is embodied to perform a first run-through of the measurement using the first membrane 14 and perform a second run-through of the measurement using the second membrane 14, wherein the MEMS sensor is embodied to perform differential processing of a result of the first run-through and of the second run-through in order to obtain a result of the second measurement.

According to a seventeenth aspect when referring back to the sixteenth aspect, the first sensitivity and the second sensitivity can form a quotient of the larger value and the smaller value, which is at least 1.1 and at most 10.

According to an eighteenth aspect, a MEMS sensor can have the following features: a substrate 12; a membrane 14 that is suspended from the substrate 12; and an evaluation device 18 which is configured to alternately in time perform a reference measurement based on an unresonant evaluation of a membrane position and perform a measurement based on a resonant frequency $f_0$ of the membrane 14.

According to a nineteenth aspect when referring back to the eighteenth aspect, the MEMS sensor can be configured to obtain a measurement result 26 on the basis of the measurement, wherein the evaluation device 18 can be embodied to determine an environmental influence that acts on the membrane 14 on the basis of the reference measurement, wherein the evaluation device 18 is embodied to take account of the environmental influence such that an influence on the measurement result 26 by the environmental influence is at least partly compensated.

According to a twentieth aspect when referring back to the eighteenth aspect, the evaluation device 18 can be embodied to provide on the basis of the reference measurement an information item in respect of an ambient pressure P that acts on the membrane 14, wherein the evaluation device 18 can be embodied to take account of an influence of the ambient pressure P on the resonant frequency $f_0$ of the membrane 14 during the measurement.

According to a twenty-first aspect, a MEMS sensor can have the following features: a substrate 12; a membrane 14 that is suspended from the substrate 12; and an evaluation device 18 which is configured to perform a measurement using a deflection 14' of the membrane 14; wherein the evaluation device 18 can be embodied to perform a first implementation of the measurement with a first membrane sensitivity of the membrane 14 and a second implementation of the measurement with a second membrane sensitivity of the membrane 14 or of a further membrane 14 in order to obtain a combined result by combining a result of the first implementation and a result of the second implementation.

According to a twenty-second aspect when referring back to the twenty-first aspect, the evaluation device 18 can be embodied to apply a first changeable electric bias voltage $U_1$ to the membrane 14 for the first implementation in order to obtain the first membrane sensitivity and to apply a second electric bias voltage $U_2$ to the membrane 14 for the second implementation in order to obtain the second membrane sensitivity.

According to a twenty-third aspect when referring back to the twenty-first aspect, the membrane 14 can be a first membrane $14_1$ which has a first sensitivity in respect of a constituent $34_1$ of a fluid, wherein the MEMS sensor further can have a second membrane 142 that has a second sensitivity in respect of the constituent $34_2$ of the fluid; wherein the MEMS sensor is embodied to perform the first implementation of the measurement using the first membrane $14_1$ and perform the second implementation of the measurement using the second membrane $14_2$, wherein the MEMS sensor is embodied to perform differential processing of a result of the first implementation and the second implementation in order to obtain the combined result.

According to a twenty-fourth aspect when referring back to the twenty-first aspect, the first membrane sensitivity and the second membrane sensitivity can form a quotient of the larger value and the smaller value, which is at least 1.1 and at most 10.

According to a twenty-fifth aspect when referring back to the twenty-first aspect, the evaluation device 18 can be embodied to take account of an environmental influence P, T that acts on the membrane 14 such that an influence on a measurement result 26 of the measurement by the environmental influence P, T is at least partly compensated.

According to a twenty-sixth aspect, a method for providing a MEMS sensor can include the following steps: providing a substrate 12; hanging a membrane 14 on the substrate 12 such that the resonant frequency $f_0$ of said membrane is influenced by an ambient pressure P; and arranging an evaluation device 18 such that the latter is configured to perform a measurement that is based on the resonant frequency $f_0$ of the membrane 14 in order to obtain a measurement result 26; such that the evaluation device 18 is embodied to take account of the ambient pressure P such that an influence on the measurement result 26 by the ambient pressure P is at least partly compensated.

According to a twenty-seventh aspect, a method for providing a MEMS sensor can include the following steps: providing a substrate 12; hanging a membrane 14 on the substrate 12; and arranging an evaluation device 18 such that the latter is configured to alternately in time perform a reference measurement based on an unresonant evaluation of a membrane position and perform a measurement based on a resonant frequency $f_0$ of the membrane 14.

According to a twenty-eighth aspect, a method for providing a MEMS sensor can include the following steps: providing a substrate 12; hanging a membrane 14 on the substrate 12; arranging an evaluation device 18 such that the latter is configured to perform a measurement using a deflection 14' of the membrane 14; and configuring the evaluation device 18 such that the latter is configured to perform a first implementation of the measurement with a first membrane sensitivity of the membrane 14 and a second implementation of the measurement with a second membrane sensitivity of the membrane 14 or of a further membrane $14_2$ and to obtain a combined result by combining a result of the first implementation and a result of the second implementation.

According to a twenty-ninth aspect, a method for measuring a fluid constituent with a fluid sensor having a membrane 14 that is suspended from a substrate 12 can include the following steps: contacting the membrane 14 with a fluid such that the membrane 14 adsorbs a fluid constituent; capturing a resonant frequency $f_0$ of the membrane 14; taking account of an ambient pressure P on the resonant frequency $f_0$ in order to obtain a corrected resonant frequency $f_0$; and determining a property of the fluid constituent on the basis of the corrected resonant frequency $f_0$.

Although some aspects have been described in association with a device, it goes without saying that these aspects also constitute a description of the corresponding method, and so a block or a component of a device should also be understood as a corresponding method step or as a feature of a method step. Analogously thereto, aspects that have been described in association with or as a method step also constitute a description of a corresponding block or detail or feature of a corresponding device.

Depending on certain requirements for implementation, exemplary embodiments of the invention can be implemented in hardware or in software. The implementation can be carried out using a digital storage medium, for example a floppy disk, a DVD, a Blu-ray disc, a CD, a ROM, a PROM, an EPROM, an EEPROM or a flash memory, a hard disk drive or any other magnetic or optical storage, on which electronically readable control signals are stored, said electronically readable control signals being able to interact or interacting with a programmable computer system in such a way that the respective method is carried out. Therefore, the digital storage medium may be computer-readable. Thus, some exemplary embodiments according to the invention comprise a data medium which has electronically readable control signals that are able to interact with a programmable computer system in such a way that one of the methods described herein is carried out.

In general, exemplary embodiments of the present invention can be implemented as a computer program product with a program code, with the program code being effective to the effect of carrying out one of the methods when the computer program product is executed on a computer. By way of example, the program code may also be stored on a machine-readable medium.

Other exemplary embodiments comprise the computer program for carrying out one of the methods described herein, wherein the computer program is stored on a machine-readable medium.

Expressed differently, an exemplary embodiment of the method according to the invention is consequently a computer program which has a program code for carrying out one of the methods described herein when the computer program is executed on a computer. Consequently, a further exemplary embodiment of the methods according to the invention is a data medium (or a digital storage medium or a computer-readable medium), on which the computer program for carrying out one of the methods described herein is recorded.

Consequently, a further exemplary embodiment of the method according to the invention is a data stream or a sequence of signals which represents the computer program for carrying out one of the methods described herein. By way of example, the data stream or the sequence of signals can be configured to the effect of being transferred by way of a data communication link, for example by way of the Internet.

A further exemplary embodiment comprises a processing device, for example a computer or a programmable logic component, which is configured or adapted to the effect of carrying out one of the methods described herein.

A further exemplary embodiment comprises a computer on which the computer program for carrying out one of the methods described herein is installed.

In some exemplary embodiments, a programmable logic component (for example a field-programmable gate array, an FPGA) can be used to perform some or all functionalities of the methods described herein. In the case of some exemplary embodiments, a field-programmable gate array can interact with a microprocessor in order to perform one of the methods described herein. In general, the methods are carried out on the part of any hardware apparatus in some exemplary embodiments. This may be universally employable hardware such as a computer processor (CPU) or hardware that is specific to the method, such as e.g. an ASIC.

The above-described exemplary embodiments only represent an illustration of the principles of the present invention. It is understood that modifications and variations of the arrangements and details described herein will be clear to other persons skilled in the art. Therefore, it is intended that the invention is only limited by the scope of protection of the following patent claims and not by the specific details that were presented on the basis of the description and the explanation of the exemplary embodiments herein.

What is claimed is:
1. A MEMS sensor comprising:
a substrate;
a membrane that is suspended from the substrate, a resonant frequency of said membrane being influenced by an ambient pressure that acts on the membrane; and
an evaluation device which is configured to perform a first measurement based on the resonant frequency of the membrane to obtain a measurement result; and
wherein the evaluation device is configured to at least partly compensate an influence of the ambient pressure on the measurement result.

2. The MEMS sensor as claimed in claim 1, wherein the evaluation device is configured to at least partly compensate an influence of an ambient temperature acting on the membrane on the measurement result.

3. The MEMS sensor as claimed in claim 1, wherein the MEMS sensor is configured to perform a reference measurement before or after the first measurement to determine the ambient pressure that acts on the membrane and to provide a result of the reference measurement of the evaluation device.

4. The MEMS sensor as claimed in claim 1, wherein the evaluation device is configured to determine the ambient pressure based on a deflection of the membrane.

5. The MEMS sensor as claimed in claim 1, wherein the evaluation device is further configured to alternately in time perform a reference measurement based on an unresonant evaluation of a membrane position and perform the first measurement.

6. The MEMS sensor as claimed in claim 5, wherein the evaluation device is configured to use a result of the reference measurement to determine the ambient pressure and to perform a calibration with respect to the first measurement.

7. The MEMS sensor as claimed in claim 1, wherein the measurement result depends on an ambient fluid that interacts with the membrane, wherein the evaluation device is configured to resonantly excite the membrane to obtain an information item with respect to the ambient fluid.

8. The MEMS sensor as claimed in claim 1, wherein the evaluation device is embodied to take account of a concentration of a constituent of a fluid that interacts with the membrane on the basis of the rule $$\Delta f(P,T,PPM) = \Sigma_{i=0}^{n} \Sigma_{j=0}^{n} \Sigma_{k=0}^{n} a_{i,j,k} P^{i} T^{j} PPM^{k},$$

where $\Delta f$ denotes a shift of the resonant frequency of the membrane obtained by the influence of an ambient temperature and the ambient pressure and $a_{i,j,k}$ denotes polynomial coefficients.

9. The MEMS sensor as claimed in claim 1, wherein the evaluation device is configured to provide a measurement signal based on a reference measurement for determining the ambient pressure and based on the first measurement, and the measurement signal has an information item with respect to the ambient pressure, an ambient temperature, and a fluid that interacts with the membrane.

10. The MEMS sensor as claimed in claim 1, wherein the membrane is configured to facilitate adsorption of a constituent of a fluid at the membrane, wherein the adsorption of the constituent causes a change in a mass of the membrane bringing about a resonance shift of a natural frequency of the membrane, and wherein the evaluation device is configured to output a measurement signal that has an information item with respect to the resonance shift.

11. The MEMS sensor as claimed in claim 10, wherein the membrane is a first membrane and the MEMS sensor has at least one second membrane, wherein the first and second membrane are configured for an adsorption of different constituents of the fluid.

12. The MEMS sensor as claimed in claim 1, wherein the MEMS sensor is formed in absence of a heating element for heating the membrane to reverse diffusion of a constituent of a fluid into the membrane.

13. The MEMS sensor as claimed in claim 1, wherein the evaluation device is configured to apply a changeable electric bias voltage to the membrane to set a changeable natural frequency of the membrane.

14. The MEMS sensor as claimed in claim 13, wherein the evaluation device is configured to change the changeable electric bias voltage based on a result of the first measurement.

15. The MEMS sensor as claimed in claim 13, wherein the evaluation device is configured to perform a reference measurement for determining the ambient pressure at a first value of the changeable electric bias voltage to obtain a first partial result and perform a further first measurement with a second value of the changeable electric bias voltage to obtain a second partial result, wherein the MEMS sensor is further configured to perform differential processing of the first partial result and of the second partial result to obtain a result of a second measurement.

16. The MEMS sensor as claimed in claim 1, wherein the membrane is a first membrane which has a first sensitivity in respect of a constituent of a fluid, and the MEMS sensor further has a second membrane which has a second sensitivity in respect of the constituent of the fluid; and
wherein the MEMS sensor is embodied to perform a first run-through of the first measurement using the first membrane and perform a second run-through of the first measurement using the second membrane, wherein the MEMS sensor is configured to perform differential processing of a result of the first run-through and of the second run-through to obtain a result of a second measurement.

17. The MEMS sensor as claimed in claim 16, wherein the first sensitivity and the second sensitivity form a quotient of a larger value and a smaller value, which is at least 1.1 and at most 10.

18. A MEMS sensor comprising:
a substrate;
a membrane that is suspended from the substrate; and
an evaluation device configured to alternately in time perform a reference measurement based on an unresonant evaluation of a membrane position and perform a first measurement based on a resonant frequency of the membrane.

19. The MEMS sensor as claimed in claim 18, configured to obtain a measurement result based on the first measurement, wherein the evaluation device is configured to determine an environmental influence that acts on the membrane on the basis of the reference measurement, and wherein the evaluation device is further configured to at least partly compensate the environmental influence on the measurement result.

20. The MEMS sensor as claimed in claim 18, wherein the evaluation device is configured to provide an information item with respect to an ambient pressure that acts on the membrane based on the reference measurement, and wherein the evaluation device is configured to take account of an influence of the ambient pressure on the resonant frequency of the membrane during the first measurement.

21. A MEMS sensor comprising:
a substrate;
a membrane that is suspended from the substrate; and
an evaluation device configured to perform a measurement using a deflection of the membrane;
wherein the evaluation device is configured to perform a first implementation of the measurement with a first membrane sensitivity of the membrane and a second implementation of the measurement with a second membrane sensitivity of the membrane or of a further membrane to obtain a combined result by combining a result of the first implementation and a result of the second implementation.

22. The MEMS sensor as claimed in claim 21, wherein the evaluation device is embodied to apply a first changeable electric bias voltage to the membrane for the first implementation to obtain the first membrane sensitivity and to apply a second electric bias voltage to the membrane for the second implementation to obtain the second membrane sensitivity.

23. The MEMS sensor as claimed in claim 21, wherein the membrane is a first membrane which has a first sensitivity in respect of a constituent of a fluid, and the MEMS sensor further has a second membrane that has a second sensitivity in respect of the constituent of the fluid; and
wherein the MEMS sensor is configured to perform the first implementation of the measurement using the first membrane and is configured to perform the second implementation of the measurement using the second membrane, wherein the MEMS sensor is configured to perform differential processing of a result of the first implementation and the second implementation to obtain the combined result.

24. The MEMS sensor as claimed claim 21, wherein the first membrane sensitivity and the second membrane sensitivity form a quotient of a larger value and a smaller value, which is at least 1.1 and at most 10.

25. The MEMS sensor as claimed in claim 21, wherein the evaluation device is configured to at least partly compensate an environmental influence acting on the membrane on a result of the measurement.

* * * * *